(12) United States Patent
Harris et al.

(10) Patent No.: US 7,770,583 B2
(45) Date of Patent: Aug. 10, 2010

(54) SURGICAL DRAPE WITH EXTENSIBLE INSTRUMENT HOLDER STRAPS

(75) Inventors: Linda G. Harris, Lawrenceville, GA (US); Henry L. Griesbach, III, Clarkston, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 521 days.

(21) Appl. No.: 11/047,379

(22) Filed: Jan. 31, 2005

(65) Prior Publication Data

US 2006/0169290 A1    Aug. 3, 2006

(51) Int. Cl.
*A61B 19/00* (2006.01)
(52) U.S. Cl. .................. 128/849; 128/851; 128/853
(58) Field of Classification Search .......... 128/849, 128/850, 851, 852, 853, 854, 855
See application file for complete search history.

(56) References Cited

U.S. PATENT DOCUMENTS

| | | | |
|---|---|---|---|
| 3,881,474 A | 5/1975 | Krzewinski | |
| 3,916,887 A | 11/1975 | Kelly | |
| 3,934,715 A * | 1/1976 | Antonini et al. | 206/570 |
| 4,040,418 A | 8/1977 | Collins | |
| 4,336,806 A * | 6/1982 | Eldridge, Jr. | 604/174 |
| 4,417,710 A * | 11/1983 | Adair | 248/51 |
| 4,989,811 A * | 2/1991 | Millis et al. | 248/104 |
| 5,010,899 A | 4/1991 | Thompson | |
| 5,037,046 A * | 8/1991 | Mingledorff, Jr. | 248/106 |
| 5,097,847 A | 3/1992 | Mikhail et al. | |
| 5,345,946 A | 9/1994 | Butterworth et al. | |
| 5,352,209 A | 10/1994 | Bird et al. | |
| 5,445,165 A * | 8/1995 | Fenwick | 128/849 |
| 5,468,231 A | 11/1995 | Newman et al. | |
| 6,187,126 B1 | 2/2001 | Rothrum et al. | |
| 6,199,553 B1 | 3/2001 | Hafer et al. | |
| 6,314,959 B1 | 11/2001 | Griesbach et al. | |
| 7,533,673 B2 * | 5/2009 | Lewis et al. | 128/849 |
| 2004/0118410 A1 | 6/2004 | Griesbach et al. | |

FOREIGN PATENT DOCUMENTS

EP    0689853 A2    1/1996

* cited by examiner

*Primary Examiner*—Patricia M Bianco
*Assistant Examiner*—Camtu T Nguyen
(74) *Attorney, Agent, or Firm*—Dority & Manning, P.A.

(57) ABSTRACT

A surgical drape for use during surgery of a patient includes a sheet that is configured for covering at least a portion of the patient during surgery. At least one instrument holder strap is attached to a front surface of the drape, the strap having a first end affixed to the drape, an opposite releasable attachment end, and an elastomeric section between the affixed end and the attachment end such that the strap can be stretched to attach surgical instruments to various locations on the drape.

15 Claims, 4 Drawing Sheets

US 7,770,583 B2

SURGICAL DRAPE WITH EXTENSIBLE INSTRUMENT HOLDER STRAPS

BACKGROUND

Various types of surgical drapes have been used to keep a surgical site on a patient sterile during a surgical procedure. Traditionally, surgical drapes were linen or woven cloth, and were sterilized after each use for reuse. More recently, fabric forms a substantial part of the drape. A reinforcement area is often placed around a fenestration or an edge of such disposable surgical drapes to provide structural strength and to absorb bodily fluids from the surgical site. Many disposable drapes also include a number of layers of different materials for the drape area and reinforcement area, with each layer providing a different property to the drape. For example, spunbond fabrics, meltblown fabrics, and polymer films have been used as layers in disposable drapes.

Many different shapes of surgical drapes have been proposed, often depending upon the specific surgical procedure to be performed. For example, the shape of the drape is often particularly designed to fit around a specific surgical site on the body. In some cases, a fenestration, as mentioned above, is provided through a drape to allow medical personnel access to the surgical site, whereas the remaining sheet portion of the drape covers the rest of the body and table. Moreover, several drapes are often used in combination as a draping system or kit to cover a patient. In some cases, several rectangular drapes, often called universal drapes, are laid over the patient in a pattern providing an opening through which the medical personnel can access the surgical site while also covering the remainder of the patient's body and the table.

Nevertheless, one drawback with many conventional drapes is that various objects and tools cannot be easily positioned on top of the drapes without falling off or without becoming contaminated. In response, some drapes have been developed to maintain medical devices during a surgical procedure. For instance, a prior surgical drape that has been developed for such a purpose includes a plurality of binding strips of material attached to the upper surface of the drape for the purpose of maintaining medical devices thereon during a surgical procedure. The strips may include a fastening system that employs hook and loop type fasteners in order to engage the medical device and retain it thereon. Reference is made, for example, to U.S. Pat. No. 5,010,899 that describes a surgical drape having a plurality of binding strips of material attached to the upper surface of the drape for retaining medical devices during a surgical procedure. The strips may include a fastening system that uses Velcro® hook fasteners and an engageable loop material, or an adhesive strip for sealing the strip over onto itself. The strips are limited to a single placement on the drape and thus do not provide flexibility or adjustability.

U.S. Pat. No. 3,881,474 discloses a surgical drape that employs tabs to fasten surgical tools in place during a surgical procedure. The tabs are attached to the drape adjacent a reinforcement area around a fenestration in the drape. The tabs are attached at specific places and are not removable or adjustable, and include holes through which surgical tools or a securing cord may be passed.

Because the instrument retaining tabs and strips of prior art drapes are limited to a given set position on their respective drapes, the surgical procedures that are performed with a particular drape may be limited. Thus, different drapes are necessary for different surgical procedures on different parts of the body. This requires the hospital or healthcare facility to stock various types of drapes, which can be expensive and generates inventory issues. Furthermore, since drape design typically follows advances in new surgical procedures, specifically designed drapes may not be immediately available for new procedures.

A need thus exists in the art for surgical drapes utilizing versatile and efficient instrument holding devices that allow the drape to be used for various surgical procedures without inhibiting the surgeon's ability to perform various procedures.

SUMMARY

Various features and advantages of the invention will be set forth in the following description, or may be obvious from the description, or may be learned from practice of the invention.

The present invention provides a surgical drape for use during surgery of a patient, the drape having a sheet configured for covering at least a portion of the patient. At least one instrument holder strap is attached to a front surface of the drape. In a particular embodiment, the holder strap has a first end attached to the drape and an opposite attachment end configured for releasably attaching to the drape or a portion of the holder strap. The attachment end may include a section of non-elastomeric material. In a particular embodiment, the attachment end includes an adhesive tape section. However, other attachment mechanisms may also be used. The holder strap further includes an elastomeric section between the end that is attached to the drape and the releasable attachment end such that the holder strap can be stretched to attach surgical instruments at various locations on the drape.

In a particular embodiment, the holder strap has a length so as to be disposed over the surgical instrument with the attachment end being secured directly to the surface of the drape. For example, an adhesive tape section may be used that has a sufficient length and amount of adhesive applied to at least one side thereof for this purpose. Alternately, the holder strap may have a length so as to fold over a surgical instrument with the tape section attaching directly to a section of the strap without attaching to surface of the drape. Still, the tape section may have adhesive on both sides to also attach directly to the surface of the drape.

In other embodiments, the holder strap may include hook material at the attachment end that can releasably fasten to the drape material itself (particularly a nonwoven material), to loop element patches or areas on the drape, or to the holder strap itself. For example, an array of hook elements may be provided opposite the side of the adhesive tape section, or in place of the adhesive tape section, or in combination with adhesive tape sections. The combination of adhesive tape and hook material provides versatility in fastening options that may be desired according to end-user preferences or need, particularly when adhesive attachment may be compromised, i.e., due to surface contamination by liquid.

It may be desired to also utilize a release liner material disposed over the adhesive portions of the tape section. This liner is manually peeled from the adhesive prior to use of the holder strap. A finger grip portion may be defined between the adhesive tape section and the release liner. For example, the release liner may extend beyond the end of the tape section and define a tab that is readily grasped by the clinician to remove the liner. Alternately, a portion of the end of the tape section may be free of adhesive so as not to stick to the release liner. This configuration may be desired in that the non-adhesive end allows for a convenient means for the clinician to grasp and reposition the holder strap after initial attachment to the drape. The release liner may be applied to one or both sides of the adhesive tape section depending on the arrangement of the adhesive sides.

In a particular configuration, the elastomeric section of the holder strap includes one or more generally elastomeric materials with an end thereof attached directly to the drape surface by any suitable attaching means. An adhesive tape section may be directly adjacent to the elastomeric section, or may be separated by another material. The adhesive tape section may be formed of the same material as the elastomeric section and have an adhesive material applied to one or both sides. In this configuration, the tape section may also have a degree of elasticity, or be rendered inelastic by the adhesive material. Alternatively, the tape section may be formed from one or more different materials and attached to the elastomeric section.

Surgical drapes typically include a fenestration through which a surgical procedure is performed, and a reinforcement material panel disposed around the fenestration. With this type of drape, one or more of the instrument holder straps may be affixed adjacent an edge of the reinforcement panel, and have a combination of length extensibility to generally provide coverage of the area of the drape circumscribed by the reinforcement panel. Any arrangement of the straps may be provided for this purpose. For example, a strap may be provided at each corner or along each side of a rectangular or square reinforcement panel. Multiple straps may be positioned around the circumference of the reinforcement panel in any desired pattern. In this way, the surgical team is assured that instruments may be positioned at any location on the reinforcement panel.

DETAILED DESCRIPTION

Figure 1:
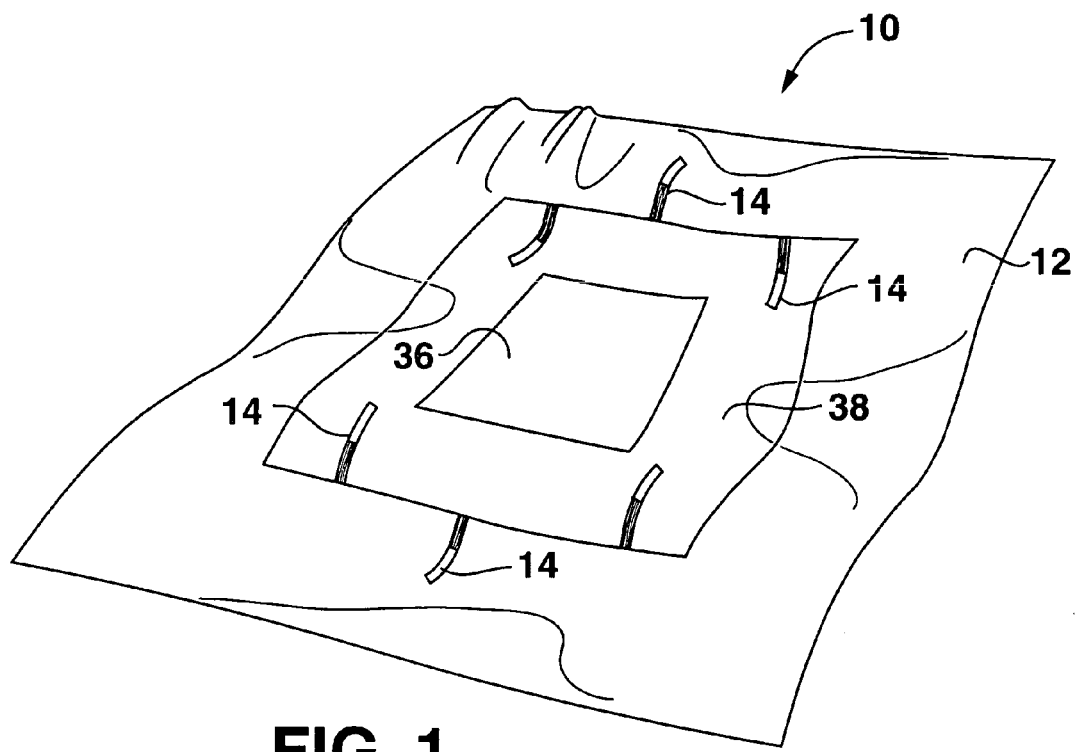
FIG. 1 is a perspective view of an exemplary embodiment of a surgical drape in accordance with the present invention with a plurality of instrument holder straps disposed around a reinforcement panel.

Reference will now be made in detail to one or more embodiments of the invention, examples of which are graphically illustrated in the drawings. The embodiments are provided by way of explanation of the invention, and not meant as a limitation of the invention. For example, features illustrated or described as part of one embodiment may be utilized with another embodiment to yield still a further embodiment. It is intended that the present invention include these and other modifications and variations.

As used herein, "attach" or "attached" refer to the bonding, joining, adhering, connecting, or the like, of two elements. Two elements may be considered attached together when they are bonded directly to one another or indirectly to one another, such as when each is directly attached to an intermediate element.

"Elastomeric" refers to a material or composite that can be extended or elongated by at least 25% of its relaxed length and that will recover, upon release of the applied force, at least 10% of its elongation. It is generally preferred that the elastomeric material or composite be capable of being elongated by at least 100%, and recover at least 50% of its elongation. An elastomeric material thus may be considered "stretchable" or "extensible."

"Nonwoven web" refers to a web that has a structure of individual fibers or filaments that are interlaid, but in an identifiable repeating manner. Nonwoven webs or fabrics have been formed from many processes known to those skilled in the art, such as meltblowing processes, spunbonding processes, bonded carded web processes, and so forth. The basis weight of nonwoven fabrics is usually expressed in ounces of material per square yard (osy) or grams per square meter (gsm), and the fiber diameters are usually expressed in microns.

Surgical drapes formed in accordance with the present invention can generally possess any of a variety of sizes and shapes, depending on the particular use of the drape and its desired properties. For example, certain surgical drape configurations are described in U.S. Pat. No. 6,055,987, which is incorporated herein by reference for all purposes. Features of conventional drapes are discussed generally herein, but need not be described in detail for a complete understanding of drapes incorporating the novel instrument holder straps according to the invention.

Referring to FIG. 1, a surgical drape 10 is illustrated. The drape 10 includes a base sheet 12 that may be formed from one or more materials. For example, base sheet 12 may be formed from one or more nonwoven layers, adhesive layers, film layers, and so forth. The sheet 12 may be hydrophilic or hydrophobic, and may be chemically treated to achieve desired water absorbency properties. In a particular embodiment, the base sheet 12 may be a nonwoven surface layer joined to a barrier layer by a meltblown adhesive layer. The nonwoven surface layer may be a spunbond propylene material sheet with a basis weight of about 20 gsm and having been bonded by a repeating pattern of discretely fused spaced apart bonds. The meltblown adhesive layer may be made form an amorphous polyolefin applied to the spunbond material at a rate of, for example, 3 gsm. The barrier layer may be a polyethylene and calcium carbonate film of about 1.5 mils thick. The film is stretched in one direction prior to lamination to the spunbond by the meltblown adhesive layer. The film provides an impermeable barrier to aqueous fluids and alcohol solutions; the inclusion of the calcium carbonate and subsequent stretching improving moisture vapor permeability.

Figure 2:
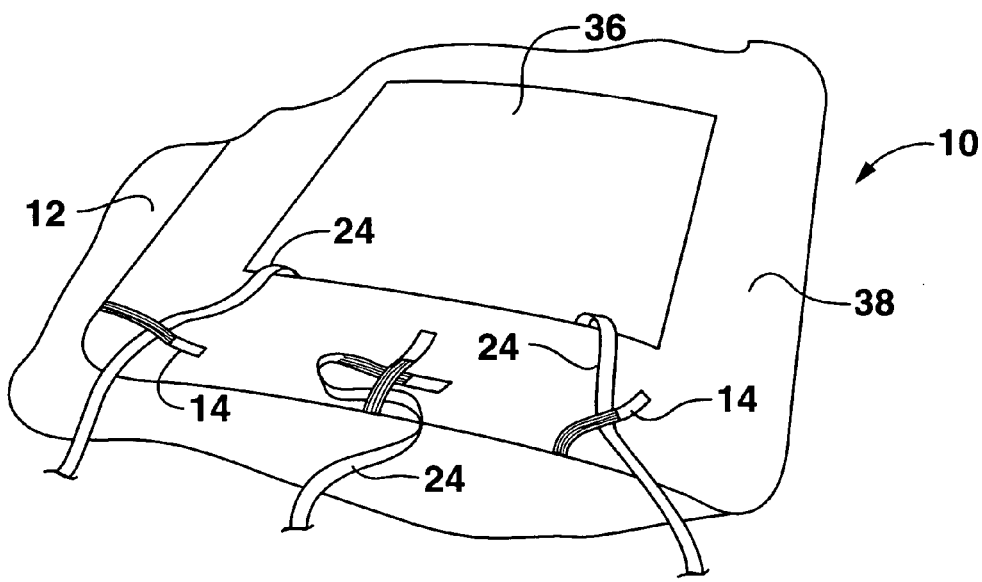
FIG. 2 is a perspective view of the embodiment of FIG. 1 wherein the instrument holder straps are in use to retain a plurality of surgical tubes relative to a fenestration.

The drape 10 may include a fenestration opening 36 that is placed over the surgical site, wherein the surgical procedure is performed through the fenestration 36, as illustrated in FIG. 2. The fenestration can have any desired shape and dimensions.

A separate material panel 38 may be attached to the base sheet 12 around the fenestration 36. In this configuration, the sheet 12 includes the panel 38 as a component thereof. This panel 38 may surround the fenestration 36, as illustrated in FIGS. 1 and 2, or be disposed along one or more sides of the fenestration 36. The panel 38 is generally referred to as a "reinforcement panel" and has properties that differ from the base sheet 12. For example, the reinforcement panel 38 may be an absorbent multi-layered nonwoven fabric. One or more of the layers may be a film. The panel 38 may be hydrophilic or hydrophobic, and may be chemically treated to achieve a desired absorbency property. In a particular embodiment, the panel 38 is a spunbond layer attached to a middle layer of a meltblown material, which is further attached to a backing layer of impervious film. This configuration allows for the reinforcement of the areas around the fenestration 36, provides fluid absorption, and ensures a fluid impervious barrier.

It should be understood that drape 10 may be formed entirely of the base sheet 12 without an additional reinforcement panel, or the drape 10 may be formed entirely of a material used for the reinforcement panel.

As depicted in FIGS. 1 and 2, the drape 10 includes one or more instrument holder straps 14. These straps 14 are intended to hold any manner of surgical instrument 24 relative to the surface of the sheet 12 or reinforcement panel 38. The term "surgical instrument" is intended to include any one or combination of devices used in surgical procedures, including but not limited to, fiber optical cords, endoscopic tubing, cords for implements, smoke evacuator tubing, irrigation/aspiration tubing, sharps, and the like. The straps 14 provide the surgical team with a means to securely locate the instruments for actual use during the procedure, as illustrated in FIG. 2, or to store the instruments on the drape 10 when the instruments are not in use. Use of the straps 14 prevent the surgical instruments 24 from sliding off of the sterile field present during surgery.

In the illustrated embodiments of FIGS. 1 and 2, the instrument holder straps 14 are attached to the sheet 12 generally adjacent the edges of the reinforcement panel 38. This may be desired in that the straps 14 can provide coverage (for holding instruments) of the area of the sheet 12 circumscribed by the reinforcement panel 38. It should be appreciated, however, that the straps may be attached to any desired location on the sheet 12, and are not limited to use around a fenestration 36 or adjacent a reinforcement panel 38.

Figure 4A:
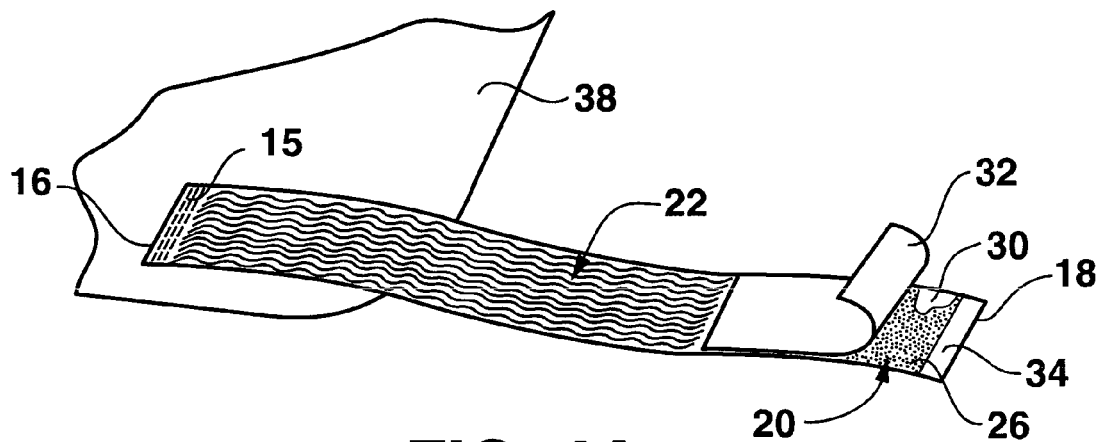
FIG. 4A is a perspective view of an alternate exemplary embodiment of an instrument holder strap in accordance with the present invention.
Figure 4B:
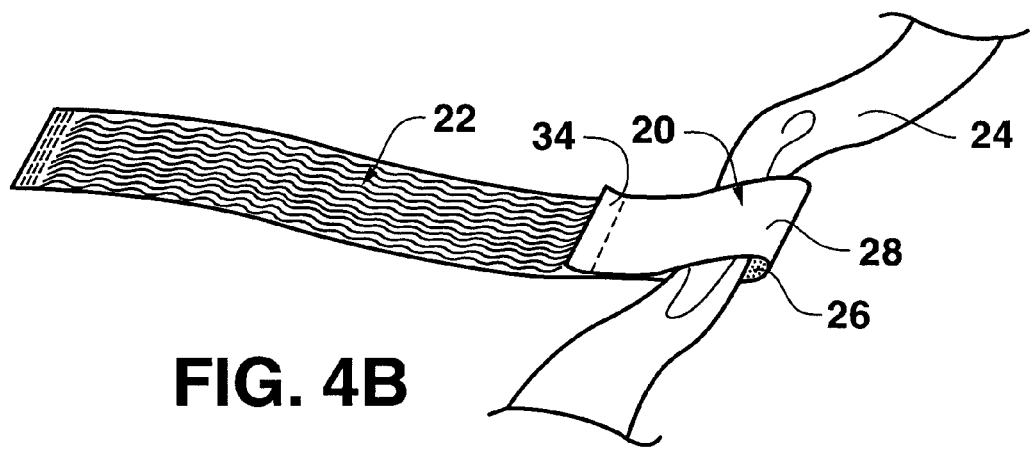
FIG. 4B is an operational view of the instrument holder strap of FIG. 4A.
Figure 4C:
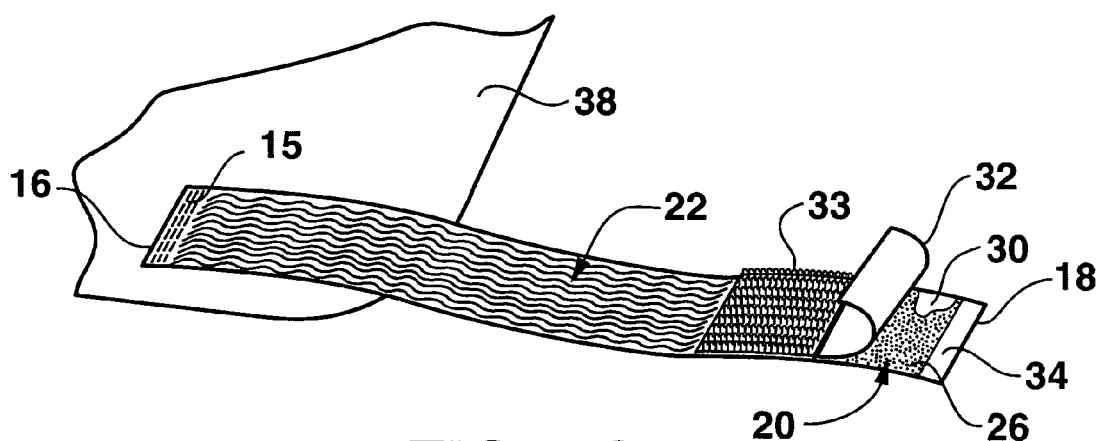
FIG. 4C is a perspective view of yet a different embodiment of an instrument holder strap according to the invention.
Figure 5:
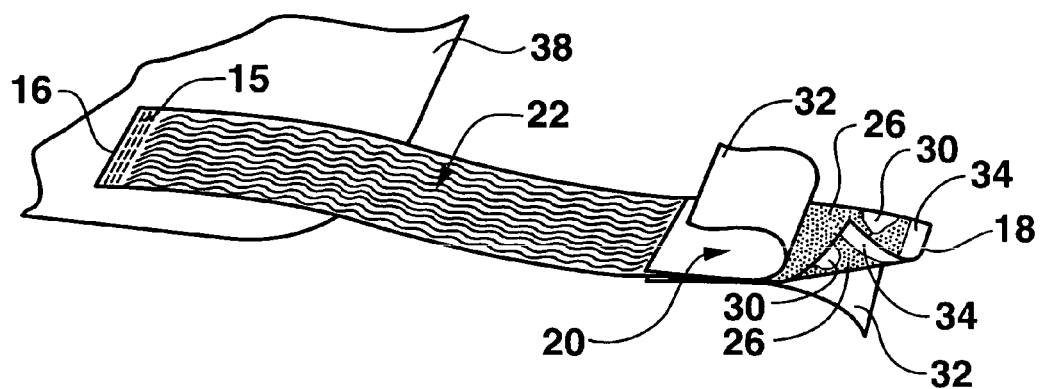
FIG. 5 is a perspective view of an alternate exemplary embodiment of an instrument holder strap in accordance with the present invention.

Referring to FIGS. 3 through 5, the illustrated embodiment of the holder straps 14 include a first end 16 secured to the reinforcement panel 38 along a bond site 15. It should be appreciated that the first end 16 need not be attached to the reinforcement panel 38, but may be attached at any desired location on the drape 10. The first end 16 may be attached by any conventional manner, including welding, adhesives, sonic bonds, thermal bonds, and so forth.

The holder straps 14 include an opposite attachment end 20 that is configured for releasable attachment to the sheet 12, reinforcement panel 38, or another section of the strap 14. An elastomeric section 22 is provided between the end 16 secured to the sheet 12 and the attachment end 20, as discussed in greater detail below. Various mechanisms may be incorporated into the attachment end 20 to render the end releasably attachable, including releasable adhesives, hook material, and so forth. In the illustrated embodiments of FIGS. 3A 4A, 4B, and 5, the attachment end 20 includes an adhesive tape section that may be formed of any conventional material having an adhesive 26 applied to one or both sides. Desirably, the adhesive may be selected so as to be readily releasable from the reinforcement panel 38 or other portions of the sheet 12 so that the surgical team may easily reposition the holder straps.

Desirably, a release liner 32 is disposed over the sides of the adhesive tape section 20 having the adhesive 26 applied thereto. This liner 32 protects the adhesive 26 and is manually peeled from the adhesive prior to use of the holder strap 14. A finger grip tab portion 34 may be defined between the adhesive tape section 20 and the release liner 32 to aid in grasping and peeling the release liner 32 from the adhesive 26. For example, the release liner 32 may extend beyond an end 18 of the tape section and define a tab that is readily grasped by the clinician to remove the liner 32. Alternately, as illustrated in the figures, a portion of the end of the tape section 20 may be free of adhesive so as not to stick to the release liner 32. This configuration may be desired in that the non-adhesive end 18 provides a convenient means for the clinician to grasp and reposition the holder strap 14 after initial attachment to the drape 10. The release liner 32 may be applied to one or both sides of the adhesive tape section 20 depending on the arrangement of the adhesive 26.

In a particular embodiment, the adhesive tape section 20 has a sufficient length and amount of adhesive 26 applied to at least one side so that the strap 14 can be disposed over a surgical instrument 24 with the tape section 20 attached directly onto the surface of the drape 10 without folding the strap 14, as illustrated in FIG. 2.

Figure 3A:
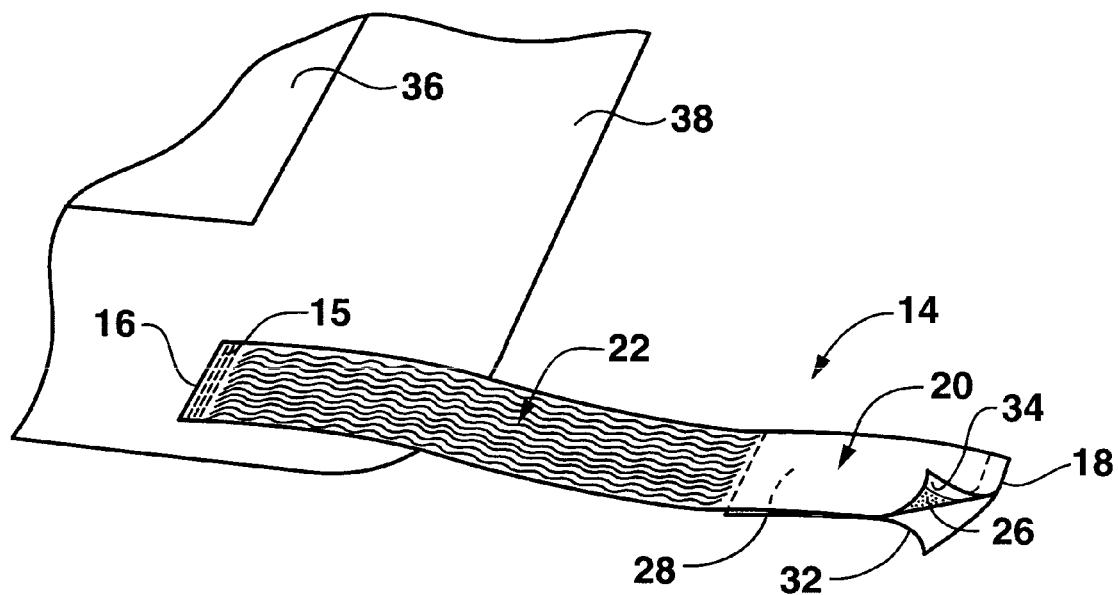
FIG. 3A is a perspective view of an exemplary embodiment of an instrument holder strap according to the invention.
Figure 3B:
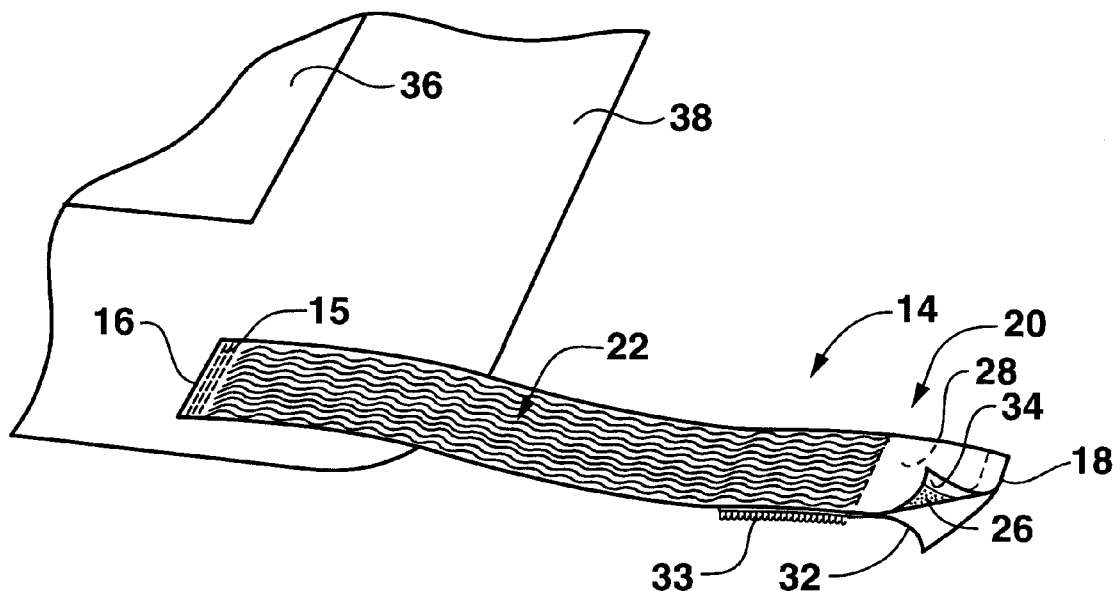
FIG. 3B is a perspective view of still another embodiment of an instrument holder strap in accordance with the invention.

With the embodiment of FIG. 3A, the orientation of the holder strap 14 is such that the first end 16 is attached to the reinforcement panel 38 and the adhesive 26 is applied to an underside (facing the drape) surface 28 of the adhesive tape section 20. This embodiment would be useful in holding a surgical instrument on a portion of the drape 10 outboard of the reinforcement panel 38.

Alternately, the tape section 20 may have a length so as to fold over a surgical instrument 24 and attach to itself or another section of the strap 14 without directly attaching to surface of the drape 10. For example, referring to FIGS. 4A and 4B, adhesive 26 is applied to an outward side 30 (facing away from the drape) and is covered by a release liner 32. To secure a surgical instrument 24, the tape section 20 may be folded over as shown in FIG. 4B and applied directly against another portion of the holder strap 14, thus creating a loop for the instrument 24. Although not depicted in the figures, the opposite side 28 of the adhesive tape section 20 could also have an adhesive applied thereto such that the "loop" could be secured in position against the drape 10.

It should be appreciated that any embodiment of the holder straps 14 may also be twisted to provide additional operational configurations of the holder straps. For example, the embodiment of FIG. 3A may be twisted along the elastomeric section 22 to operate substantially the same as the untwisted embodiment of FIG. 4A.

As mentioned, the attachment end 20 may include other releasable attaching devices alone or in combination with the adhesive section 26. A particularly useful attaching device is a hook material that attaches to a complimentary loop material, or similarly functioning material. For example, in the embodiment of FIG. 3B, the attachment end includes a section 33 of hook material adjacent the adhesive section 26. The hook material may attach directly to the sheet 12, reinforcement panel 38, or other portions of the strap 14. Patches or areas of loop material may be applied to portions of the drape 12 where likely attachment of the strap 14 is anticipated. The hook material 33 may serve as the primary attachment means, or in combination with the adhesive 26. It should also be appreciated that the attachment end 20 may include only hook material 33 (without adhesive 26).

FIG. 4C is a view of an alternate embodiment similar to FIG. 4A with the addition of hook material 33 adjacent to the adhesive section 26. The hook material may serve to secure the attachment end 20 directly to the strap 14, as in FIG. 4B, or to the drape 12 and reinforcement panel 38.

FIG. 5 illustrates a particularly versatile embodiment of an instrument holder strap having adhesive 26 applied to both sides 28, 30 of the adhesive tape section 20. Respective release liners 32 are also applied to the adhesive sides. It should be appreciated that it is not a requirement that both sides of the adhesive tape section 20 be exposed. The clinician may remove one or both of the release liners depending on the intended use of the holder 14.

The elastomeric section 22 of the holder strap 14 includes one or more generally elastomeric materials with an end 16 attached directly to the drape surface by any suitable attaching means. Alternatively, a non-elastic material may be attached to the end 16, which is in turn attached to the drape 10. The adhesive tape section 20 may be directly adjacent to the elastomeric section and attached directly thereto, or may be separated by another material. The adhesive tape section 20 may be formed of the same materials as the elastomeric section 22 such that the boundary between the two sections is the extent of the adhesive 26. In this configuration, the tape section 20 may also have a degree of elasticity, or the tape section 20 may be rendered inelastic by the adhesive material 26. Alternatively, the tape section 20 may be formed from one or more different materials and attached to the elastomeric section.

The elastomeric section 22 may be formed of any one or combination of materials known to those skilled in the art that render the section with a desired degree of elasticity. The length and desired elasticity of the section 22 will be a factor of the location of the holder straps 14, size of the drape 10, surgical procedures, and so forth. Generally, the elastomeric section 22 should have a length and elasticity so as to be stretchable to various locations around the fenestration 36 such that a single holder strap 14 provides coverage to an extended area of the drape as compared to a non-elastomeric strap. The elasticity of the section 22 also should be selected so that the strap does not cause excessive bunching of the drape 10 when the strap is extended to its fullest stretched range. However, it is also within the scope of the invention to utilize the straps 14 to form and retain folds in the drape 10 for various purposes (i.e., to form pockets along the drape). In this case, it may be desired for the straps 14 to incorporate an elastomeric section 22 with a relatively high degree of recovery.

Figure 6:
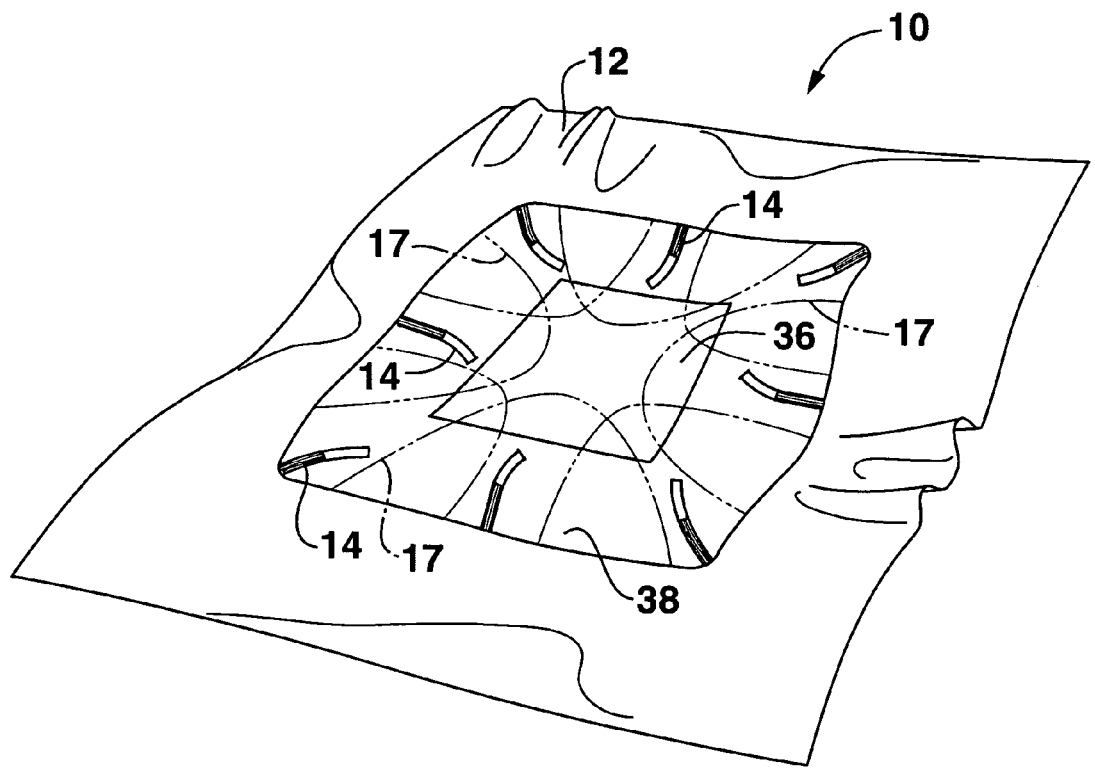
FIG. 6 is a perspective view of an exemplary embodiment of a surgical drape in accordance with the present invention, particularly illustrating coverage of a plurality of instrument holder straps.

It should be appreciated that the drape 10 according to the invention is not limited to any particular arrangement of the straps 14. For example, a strap 14 may be provided at each corner or along each side of a rectangular or square reinforcement panel 38. Multiple straps may be positioned around the circumference of the reinforcement panel 38 in any desired pattern. FIG. 6 illustrates an embodiment of a drape 10 having a pattern of the instrument holder straps 14 disposed around the perimeter of the reinforcement panel 38 such that essentially the entire area of the panel 38 is provided coverage with the straps 14. The dashed lines 17 depict the coverage areas for the individual straps 14. With this type of arrangement, the clinician may position one or more of the straps generally anywhere on the reinforcement panel 38.

It should be understood that the present invention includes various modifications that can be made to the exemplary embodiments of the surgical drape described herein as come within the scope of the appended claims and their equivalents.

What is claimed is:

1. A surgical drape for use during surgery of a patient, comprising:

a sheet configured to be laid over at least a portion of the patient during surgery;

at least one instrument holder strap attached to a front surface of the sheet, the front surface being the outermost surface of the sheet when the sheet is laid over at least a portion of the patient during surgery, said instrument holder strap comprising a first end non-releasably attached directly onto said front surface of said sheet at a permanent bond site directly between said first end and said sheet such that position of said holder strap relative to said drape is permanently fixed, and an opposite attachment end that includes a non-elastomeric section of said holder strap, said holder strap further comprising an elastomeric section between said first end and said attachment end such that said holder strap can be stretched to various locations on said drape.

2. The surgical drape as in claim 1, wherein said attachment end comprises an adhesive tape section.

3. The surgical drape as in claim 1, wherein said attachment end comprises a hook material.

4. The surgical drape as in claim 1, wherein said attachment end comprises an adhesive tape section and hook material.

5. The surgical drape as in claim 1, wherein said opposite attachment end has a sufficient length and an adhesive to be attached directly to said sheet or another portion of said holder strap.

6. The surgical drape as in claim 2, wherein said adhesive tape section comprises an adhesive on both sides.

7. The surgical drape as in claim 2, wherein said adhesive tape section comprises a release liner over an adhesive portion thereof.

8. The surgical drape as in claim 1, further comprising a non-adhesive tab section at said opposite attachment end of said instrument holder strap such that a user can grasp said non-adhesive tab section and reposition said instrument holder strap on said sheet.

9. The surgical drape as in claim 1, wherein said first end includes said elastomeric section such that said elastomeric material is attached to said sheet.

10. The surgical drape as in claim 2, wherein said adhesive tape section comprises an adhesive applied to a section of elastomeric material extending from said elastomeric section.

11. The surgical drape as in claim 9, wherein said non-elastomeric section of said holder strap is rendered non-elastomeric by a coating of adhesive material.

12. The surgical drape as in claim 1, wherein said drape further comprises a fenestration through which a surgical procedure is performed, and a reinforcement material panel disposed around said fenestration, said instrument holder strap affixed adjacent an edge of said reinforcement material panel.

13. The surgical drape as in claim 12, comprising a plurality of said instrument holder straps spaced around said reinforcement panel, said instrument holder straps having an extensibility such that the combination of instrument holder straps provide generally complete coverage of said reinforcement panel.

14. The surgical drape as in claim 13, comprising at least one said instrument holder strap affixed adjacent each edge of said reinforcement panel.

15. The surgical drape as in claim 2, wherein said adhesive tape section comprises a releasable adhesive so that said instrument holder strap is repositionable on said drape.

* * * * *